United States Patent [19]

Casciani

[11] Patent Number: 4,460,789
[45] Date of Patent: Jul. 17, 1984

[54] PROCESS FOR PREPARING ALKOXYLATES CONTAINING PRIMARY AMINE FUNCTIONS

[75] Inventor: Robert V. Casciani, Long Valley, N.J.

[73] Assignee: Sandoz, Inc., E. Hanover, N.J.

[21] Appl. No.: 387,170

[22] Filed: Jun. 10, 1982

[51] Int. Cl.³ ............................................. C07C 85/02
[52] U.S. Cl. ..................................... 564/504; 564/505
[58] Field of Search .............................. 564/504, 505

[56] References Cited

U.S. PATENT DOCUMENTS 3,110,732  11/1963  Speranza et al. .................... 564/505
4,145,307   3/1979  Krapf et al. ...................... 564/504 X
4,252,745   2/1981  Kwong et al. ..................... 564/504 X Primary Examiner—Paul F. Shaver
Attorney, Agent, or Firm—Gerald D. Sharkin; Robert S. Honor; Joseph J. Borovian

[57] ABSTRACT

The invention relates to a new process for preparing alkoxylates containing primary amine functions comprising reacting a monoalkanolamine or a polyamine compound with a carbonyl compound to form an amide- or carbamate-type condensation product, reacting said condensation product with an alkylene oxide compound to form an alkylene oxide adduct of said condensation product, and salifying the so-formed adduct under mild, acidic conditions.

19 Claims, No Drawings

PROCESS FOR PREPARING ALKOXYLATES CONTAINING PRIMARY AMINE FUNCTIONS

This invention relates to a new process for preparing alkoxylates containing primary amine functions.

Amine derivatives of polyoxyalkylene glycols are useful for preparing non-ionic and cationic emulsifiers and have use in the insecticide, wax and leather industries. In addition, they are valuable as foam stabilizers, antistatic agents, re-wetting agents, anti-oxidants and as corrosion inhibitors. The many valuable applications of the amine derivatives of polyoxyalkylene glycols suggest that other structurally similar amine derivatives would also have a variety of valuable applications and such is, indeed, the case. Thus, the primary amine function-containing alkoxylates to which this application is directed are not only valuable for each of the above-mentioned uses but, in addition, are useful as levelling agents in the dyestuff industry and for stabilizing dye preparations. Furthermore, they are especially useful as chemical intermediates in the preparation of compounds having value in water treatment processes, e.g., as scale inhibitors.

U.S. Pat. No. 3,110,732 discloses a process for preparing a primary amine basic polyether employing an alkanolamine having a primary amine group as the starting material. The alkanolamine reactant is contacted with a carbonyl compound to effect the formation of a condensation product, and this condensation product is then contacted with an alkylene oxide to effect the formation of an alkylene oxide adduct of the condensation product. The so-formed adduct is then hydrolyzed to produce the desired basic polyether. As is fairly evident, and as is readily acknowledged by the patentees, the process of U.S. Pat. No. 3,110,732 employs a well-known reaction in which a primary amine and a carbonyl compound combine or condense at the amine and carbonyl groups respectively with the exclusion of a mole of water. The purpose of this step is to effectively block the amino group so that said group will not be reactive during the oxyalkylation step. Although the utilization of the concept of blocking the amino group is employed in the instant process, it will be readily seen that such is accomplished by an entirely different chemical reaction. Thus, whereas the process of U.S. Pat. No. 3,110,732 results in an imine-type condensation product, the process of this application involves the formation of an amide- or carbamate-type condensation product.

Accordingly, it is an object of the present invention to provide a new process for preparing amine derivatives. It is another object of the present invention to provide a new process for preparing alkoxylated amine derivatives. It is still another object of the present invention to provide a new process for preparing alkoxylates containing primary amine functions. It is yet still another object to provide a commercially attractive process for preparing alkoxylates containing primary amine functions.

The attainment of the above objects is made possible by a novel three-step process comprising contacting a monoalkanolamine compound or a polyamine compound with a carbonyl compound to effect the formation of a condensation product, to which is then added an alkylene oxide compound or a mixture thereof to effect the formation of an alkylene oxide adduct of said condensation product. The so-formed adduct is ultimately salified to produce the desired final products in stable amine salt form.

More particularly, the process of the present invention comprises reacting a monoalkanolamine compound of the formula

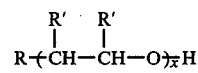

wherein R is $NH_2-$ or $NH_2-R''-$,
where R'' is methylene or dimethylene,
each R', independently, is hydrogen, methyl or ethyl, and
x is an integer 1 or 2,
or a polyamine compound of the formula,

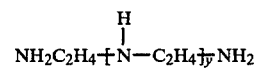

where y is 0 or an integer 1 to 3,
with a carbonyl compound of the formula

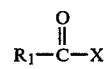

where $R_1$ is $C_{1-10}$alkyl; $C_{1-10}$alkoxy; phenyl; substituted phenyl; phenoxy; substituted phenoxy; benzyl; substituted benzyl; benzyloxy or substituted benzyloxy; and
X is $O-R_2$, where $R_2$ is hydrogen, $C_{1-10}$-alkyl, phenyl, substituted phenyl, benzyl or substituted benzyl; or a group of the formula

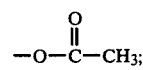

wherein substituted phenyl, phenoxy, benzyl or benzyloxy has one or two substituents independently selected from chloro, bromo, nitro, cyano and $-SO_3H$, with the proviso that when X is a group of the formula

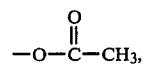

$R_1$ is $CH_3$,
at a temperature within the range of 25° to 175° C. to form an amide- or carbamate-type condensation product, reacting said condensation product with an alkylene oxide compound or a mixture thereof at an elevated temperature and pressure in the presence of a catalytic amount of an alkaline catalyst to form an alkylene oxide adduct of said condensation product, and salifying the so-formed adduct under mild, acidic conditions to effect the formation of the desired final product in stable amine salt form.

Suitable monoalkanolamines which may be employed as starting reactants in the instant process include monoethanolamine, 1-amino-2-propanol, 2-amino-1-propanol, 3-amino-1-propanol, 2-(2-aminoethoxy)ethanol, 1-amino-2-butanol, 2-amino-3-butanol and the like.

Polyamines which are suitable as starting reactants in the instant process are ethylene diamine, diethylene triamine, triethylene tetramine and tetraethylene pentamine.

Carbonyl compounds which are embraced by the above formula and may be employed in the formation of the condensation products with the monoalkanolamines or polyamines can be generally referred to as carbonates, monocarboxylic acids and esters thereof, acyl chlorides and acetic anhydride.

Preferred carbonyl compounds which may be employed in the formation of the condensation products are carbonates of the formula

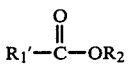

$$R_1'-\overset{O}{\underset{\|}{C}}-OR_2$$

where $R_1'$ is $C_{1-10}$ alkoxy, phenoxy, substituted phenoxy, benzyloxy or substituted benzyloxy, and
$R_2$ is $C_{1-10}$ alkyl, phenyl, substituted phenyl, benzyl or substituted benzyl.

Especially preferred carbonates of the above group are those where $R_1'$ is $C_{1-10}$ alkoxy and $R_2$ is $C_{1-10}$ alkyl, particularly diethyl carbonate.

Other preferred carbonyl compounds which may be employed in the formation of the condensation products are monocarboxylic acids and corresponding esters of the formula

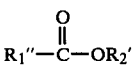

$$R_1''-\overset{O}{\underset{\|}{C}}-OR_2'$$

where $R_1''$ is $C_{1-10}$ alkyl, phenyl, substituted phenyl, benzyl or substituted benzyl, and
$R_2'$ is hydrogen, $C_{1-10}$ alkyl, phenyl, substituted phenyl, benzyl or substituted benzyl.

Especially preferred mono-carboxylic acids and corresponding esters are those where $R_1$ is $C_{1-10}$ alkyl and $R_2'$ is hydrogen or $C_{1-10}$ alkyl. A particularly preferred $C_{1-10}$ mono-carboxylic acid is acetic acid, whereas a particularly preferred ester is ethyl acetate.

Acyl chlorides which are suitable include acetyl chloride and benzoyl chloride.

The molar ratio of the reactants employed in the formation of the condensation products is dependent upon the number of primary amino groups available for reaction. Thus, when the reaction involves a monoalkanolamine and a carbonyl compound, equimolar amounts of the reactants are generally employed in the formation of the condensation product although an excess of either of the reactants may be employed, whereas when the reaction involves a polyamine and a carbonyl compound, the molar ratio of polyamine to carbonyl compound is generally 1:2. The reaction is spontaneous in nature, particularly when conducted at a moderately elevated temperature. The reaction may be conducted at a temperature within the range of 25° to 175° C., preferably within the temperature range of 25° to 160° C. If desired, an inert solvent may be added to aid the reaction or to facilitate the removal of by-products liberated by the reaction. On completion of the formation of the condensation product, any excess carbonyl compound is removed by distillation, preferably at reduced pressures, followed by recovery of the condensation product.

The condensation product formed in the above step is then reacted with an alkylene oxide compound or a mixture thereof under oxyalkylation conditions to form a condensation product-alkylene oxide adduct. The oxyalkylation reaction is conducted in the presence of a catalytic amount, e.g., from about 0.2% to 1%, preferably 0.3% to 0.75%, by weight of the total amount of reactants, including the alkylene oxide compound or mixtures thereof, of an alkaline catalyst. Catalysts which may be employed include alkali metal hydroxides, sodium ethoxide, sodium methoxide, alkali metal acetates and dimethylamine, and mixtures thereof. Preferred catalysts are the alkali metal hydroxides, more preferably sodium hydroxide and potassium hydroxide. Other types of catalysts commonly used for alkylene oxide condensation reactions may also be employed.

Optionally, a small amount of a reducing agent may be added to the condensation product to be alkoxylated to minimize discoloration of the resulting condensation product-alkylene oxide adduct. Suitable reducing agents which may be employed include sodium borohydride, lithium aluminum hydride, diborane and the like, preferably sodium borohydride.

Thus, in preparing a condensation product-alkylene oxide adduct wherein the polyoxyalkylene portion comprises a single alkylene oxide, e.g., ethylene oxide, an amount of ethylene oxide calculated to provide the desired degree of ethoxylation is introduced into the condensation product-catalyst mixture and the resulting mixture is allowed to react until the ethylene oxide is consumed, as indicated by a drop in reaction pressure. In preparing a condensation product-alkylene oxide adduct wherein the polyoxyalkylene portion comprises two types of alkylene oxides, e.g., propylene oxide and ethylene oxide moieties, an amount of propylene oxide calculated to provide the desired degree of propoxylation is introduced into the condensation product-catalyst mixture and the resulting mixture is allowed to react until the propylene oxide is consumed, as indicated by a drop in reaction pressure. A similar introduction and reaction of a calculated amount of ethylene oxide serves to provide the second block which completes the alkoxylation.

Similarly, in preparing a condensation product-alkylene oxide adduct wherein the polyoxyalkylene portion contains ethylene oxide blocks interrupted by a higher alkylene oxide block, e.g., a propylene oxide block, an amount of ethylene oxide is introduced into the condensation product-catalyst mixture until the ethylene oxide is consumed, as indicated by a drop in reaction pressure. A similar introduction and reaction of a calculated amount of propylene oxide or other alkylene oxide serves to provide the second block. Following this, ethylene oxide is again added in the desired amount to provide the third block which completes the alkoxylation.

It should be understood that each separate alkoxylation procedure serves to introduce a desired average number of alkylene oxide units per molecule of condensation product. Thus, for example, the initial reaction of a condensation product with m moles of ethylene oxide serves to effect the ethoxylation of each molecule of condensation product with ethylene oxide to an average of m ethylene oxide moieties per molecule of condensation product, although some molecules of condensation product will have become combined with more than m ethylene oxide moieties and some will have become combined with less than m.

Each alkoxylation is conducted at an elevated temperature and pressure. Suitable reaction temperatures are from about 120° C. to about 220° C., preferably 140°

C. to 200° C., and more preferably 140° C. to 180° C. A suitable reaction pressure is achieved by introducing to the reaction vessel the required amount of ethylene oxide or higher alkylene oxide, each of which has a high vapor pressure at the desired reaction temperature. The decrease in pressure serves as a measure of the degree of reaction and each alkoxylation is considered to be complete when the pressure no longer decreases with time.

For best results, it is desirable to carry out the alkoxylation under relatively moisture-free conditions and to avoid side reactions which form water. To dry the reaction vessel and connections, they must be swept out with dry, oxygen-free gas, e.g., nitrogen, before introducing the charge. The catalyst or catalyst mixture should also be dry, or substantially so. The alkylene oxides should preferably be purified to remove moisture and any impurities which are capable of entering into side reactions which yield water.

The resulting condensation product-alkylene oxide adduct is then salified by subjecting said adduct to hydrolysis under mild, acidic conditions. This results in splitting of the adduct at the point where the carbonyl and the amino groups originally combined without disturbing the alkylene oxide units added during the oxyalkylation. Besides forming the stable amine salt, hydrolysis effects a regeneration of the carbonyl compound originally employed to form the condensation product. The mild, acidic hydrolysis takes place spontaneously upon contacting the condensation product-alkylene oxide adduct with a mineral acid such as hydrochloric, hydrobromic, sulfuric and phosphoric acids, preferably hydrochloric acid, or an organic acid such as acetic, lactic, tartaric, oxalic or succinic acids. The hydrolysis may be carried out conveniently at a temperature of from −40° to 100° C., preferably at a temperature of from 10° to 30° C. The hydrolyzed reaction product is then stripped of the carbonyl compound to separate the stable amine salt.

The monoalkanolamines, polyamines and carbonyl compounds employed as starting materials in preparing the condensation products are either known and obtained by methods described in the literature, or where not known, may be obtained by methods analogous to those described in the literature.

The alkoxylates prepared by the process of this invention are all generally known and, as previously indicated, not only possess a myriad of uses themselves but are especially valuable as chemical intermediates in the preparation of compounds which are useful in water treatment processes. A particularly preferred compound for which the process of this invention is useful is 2-amino-2'-[2-hydroxyethoxy]-diethyl ether.

The following examples are for purposes of illustration only and are not intended to in any way limit the scope of the invention.

EXAMPLE 1

Preparation of the condensation product of ethanolamine and ethyl acetate

To a reaction vessel equipped with a condenser, stirrer and a thermometer was added 88.11 g. (1 mole) of ethyl acetate. With stirring, 68.01 g. (1.11 mole) of ethanolamine were added, in one portion, at which time the reaction mixture became viscous and cloudy and the temperature of the reaction mixture dropped to 3° C. Under constant stirring, the reaction mixture was gradually heated, over a three-hour period, to a temperature of 70° C. The reaction mixture was then allowed to further react for an additional 72 hours, while the temperature of the reaction mixture was maintained at 60° C. Termination of the reaction and removal of the by-product, ethanol, by flash evaporation yielded 103.12 g. of an amber colored, slightly viscous liquid of the formula

Preparation of N-acetyl-2-amino-2'-[2-hydroxyethoxy]-diethyl ether 365.0 g. of N-acetylethanolamine and 1.4 g. of potassium hydroxide (in flake form) were charged to a 1 liter flask and the reaction mixture heated to 90° C. under 28 inches of vacuum (equivalent to ~5–10 mm. of mercury). The reaction system was then purged with nitrogen to break the vacuum and the purging procedure was repeated two additional times to minimize the presence of air. The temperature and the vacuum of the reaction system were maintained at 90° C. and 28 inches, respectively, for an additional 30 minutes to remove moisture from the reaction system. After shutting the vacuum valve, the temperature of the reaction mixture was raised to 150° C., which lowered the vacuum of the reaction system to 27 inches. The vacuum of the reaction system was then broken by commencing the addition of ethylene oxide. Over a period of sixty minutes, a total of 311.8 g. of ethylene oxide was added at a rate to maintain the pressure of the reaction system at 4 lbs./sq. in., while the temperature of the resulting reaction mixture, with intermittent cooling, was maintained at 155° C. After allowing the reaction mixture to further react until the pressure of the reaction system stabilized, the reaction mixture was then cooled to 80° C., purged with nitrogen to break the vacuum and a dark reddish-brown, slightly viscous liquid of the formula

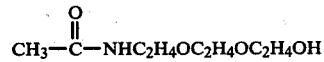

was obtained.

Hydrolysis of N-acetyl-2-amino-2'-[2-hydroxyethoxy]-diethyl ether 50 g. of 2-amino-2'-[2-hydroxyethoxy]-diethyl ether was dissolved in 250 mls. of hydrochloric acid (10%) and refluxed at 100° C. for 24 hours. Air drying of the resultant mixture for 72 hours yielded the compound, 2-amino-2'-[2-hydroxyethoxy]-diethyl ether, in stable hydrochloride salt form.

EXAMPLE 2

Preparation of the condensation product of ethanolamine and diethyl carbonate

To a reaction vessel equipped with a condenser, stirrer and a thermometer was added 61.08 g. (1.0 mole) of ethanolamine. With stirring, 118.0 g. (1.0 mole) of diethylcarbonate was added, in one portion, resulting in a slight drop in temperature of the reaction mixture. Under constant stirring, the reaction mixture was heated to 45° C. and then allowed to react for an additional 48 hours, while the temperature of the reaction mixture was maintained at 45° C. Termination of the reaction and removal of the by-product, ethanol, in vacuo yielded a yellow, slightly viscous liquid of the formula

EXAMPLE 3

Preparation of the condensation product of ethanolamine and acetic acid

To a reaction vessel equipped with a condenser, stirrer and a thermometer was added 61.08 g. (1.0 mole) of ethanolamine. With stirring, the dropwise addition of 60.05 g. (1.0 mole) of acetic acid was commenced, resulting in a rise in temperature of the reaction mixture to 60° C., at which time cooling of the reaction mixture by means of a water bath was initiated. After the addition of acetic acid was completed, the temperature of the resulting reaction mixture was heated to 160° C., at which time the formation of water began. The water generated was collected in a claisen trap and, after 9 mls. was collected (50% of theoretical), a water aspirator vacuum was applied. After the remaining 9 mls. of water was collected, the reaction was terminated and the reaction mixture was cooled to room temperature yielding a clear, yellow liquid of the formula

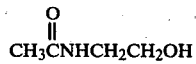

EXAMPLE 4

Following essentially the ethoxylation procedure of Example 1, and using in place of the condensation product prepared therein, an equivalent amount of the condensation products of Examples 2 and 3, the compounds, N-[β-(β'-2-hydroxyethoxy)ethoxyethyl]-ethyl carbamate and N-acetyl-2-amino-2'-[2-hydroxyethoxy]-diethyl ether, respectively, are obtained.

EXAMPLE 5

Following essentially the hydrolysis procedure of Example 1, and using in place of the diethyl ether compound prepared therein, an equivalent amount of the compounds prepared in Example 4, the stable hydrochloride salt of 2-amino-2'-[2-hydroxyethoxy]-diethyl ether is obtained in both cases.

What is claimed is:

1. A process for preparing alkoxylated amine derivatives which comprises reacting a monoalkanolamine compound of the formula $$R-(CH-CH-O)_{\overline{x}}H$$
with R' above each CH wherein R is $NH_2-$ or $NH_2-R''-$,
where R'' is methylene or dimethylene,
each R', independently, is hydrogen, methyl or ethyl and
x is an integer 1 or 2,
or a polyamine compound of the formula,

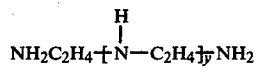

where y is 0 or an integer 1 to 3,
with a carbonyl compound of the formula

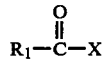

where $R_1$ is $C_{1-10}$alkyl; $C_{1-10}$alkoxy; phenyl; substituted phenyl; phenoxy; substituted phenoxy; benzyl; substituted benzyl; benzyloxy or substituted benzyloxy; and X is $O-R_2$, where $R_2$ is hydrogen, $C_{1-10}$-alkyl, phenyl, substituted phenyl, benzyl or substituted benzyl; or a group of the formula

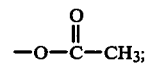

wherein substituted phenyl, phenoxy, benzyl or benzyloxy has one or two substituents independently selected from chloro, bromo, nitro, cyano and $-SO_3H$, with the proviso that when X is a group of the formula

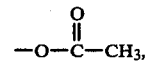

$R_1$ is $CH_3$, at a temperature within the range of 25° to 175° C. to form an amide- or carbamate-type condensation product, reacting said condensation product with an alkylene oxide compound or a mixture thereof at an elevated temperature and pressure in the presence of a catalytic amount of an alkaline catalyst to form an alkylene oxide adduct of said condensation product, and salifying the so-formed adduct under mild, acidic conditions.

2. The process according to claim 1 in which the monoalkanolamine or polyamine compound is reacted with the carbonyl compound at a temperature within the range of 25° to 160° C.

3. The process of claim 1 in which the monoalkanolamine compound is reacted with an equivalent amount of the carbonyl compound.

4. The process of claim 1 in which the polyamine compound is reacted with the carbonyl compound at a molar ratio of polyamine compound to carbonyl compound of 1:2.

5. The process of claim 3 in which the monoalkanolamine compound is selected from the group consisting of monoethanolamine, 1-amino-2-propanol, 2-amino-1-propanol, 3-amino-1-propanol, 2-(2-aminoethoxy)ethanol, 1-amino-2-butanol and 2-amino-3-butanol.

6. The process of claim 5 in which the monoalkanolamine is ethanolamine.

7. The process of claim 1 in which the carbonyl compound is of the formula

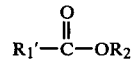

where $R_1'$ is $C_{1-10}$ alkoxy, phenoxy, substituted phenoxy, benzyloxy or substituted benzyloxy, and $R_2$ is $C_{1-10}$ alkyl, phenyl, substituted phenyl, benzyl or substituted benzyl.

8. The process of claim 7 in which $R_1'$ is $C_{1-10}$ alkoxy and $R_2$ is $C_{1-10}$ alkyl.

9. The process of claim 8 in which the carbonyl compound is diethyl carbonate.

10. The process of claim 1 in which the carbonyl compound is of the formula

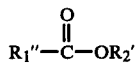

where $R_1''$ is $C_{1-10}$ alkyl, phenyl, substituted phenyl, benzyl or substituted benzyl, and $R_2'$ is hydrogen, $C_{1-10}$ alkyl, phenyl, substituted phenyl, benzyl or substituted benzyl.

11. The process of claim 10 in which $R_1''$ is $C_{1-10}$ alkyl and $R_2'$ is hydrogen or $C_{1-10}$ alkyl.

12. The process of claim 11 in which the carbonyl compound is ethyl acetate.

13. The process of claim 11 in which the carbonyl compound is acetic acid.

14. The process of claim 6 in which the carbonyl compound is ethyl acetate.

15. The process of claim 6 in which the carbonyl compound is acetic acid.

16. The process of claim 6 in which the carbonyl compound is diethyl carbonate.

17. A process for preparing a stable amine salt of 2-amino-2'-[2-hydroxyethoxy]-diethyl ether which comprises reacting ethanolamine with an equivalent amount of ethyl acetate at a temperature within the range of 25° to 175° C. to form N-acetyl ethanolamine, reacting said compound with ethylene oxide at an elevated temperature and pressure in the presence of a catalytic amount of potassium hydroxide to form an ethylene oxide adduct of said N-acetyl ethanolamine, and salifying the so-formed adduct under mild, acidic conditions.

18. The process of claim 17 wherein the ethylene oxide adduct of N-acetyl ethanolamine is salified with a mineral acid selected from the group consisting of hydrochloric acid, hydrobromic acid, sulfuric acid and phosphoric acid.

19. The process of claim 18 wherein the mineral acid is hydrochloric acid.

* * * * *